United States Patent [19]
Koteles et al.

[11] Patent Number: 5,938,592
[45] Date of Patent: Aug. 17, 1999

[54] SURGICAL SUPPORT APPARATUS WITH ADJUSTABLE RAKES AND RAKE PLATE AND METHOD OF USE

[75] Inventors: William John Koteles, Broadview Heights; Ivan George Kovacs, Lakewood; Janice Lee Rullo, Mayfield Heights, all of Ohio

[73] Assignee: Rultract, Inc., Cleveland, Ohio

[21] Appl. No.: 08/792,012

[22] Filed: Jan. 31, 1997

[51] Int. Cl.⁶ ..................................................... A61B 17/00
[52] U.S. Cl. ............................................. 600/228; 600/227
[58] Field of Search .................................. 600/213, 214, 600/215, 217, 227, 228, 229, 231, 234, 201, 235; 602/36, 37

[56] References Cited

U.S. PATENT DOCUMENTS

| | | |
|---|---|---|
| 1,048,750 | 12/1912 | Smith . |
| 1,242,688 | 10/1917 | Hawley .................................. 602/33 |
| 1,914,202 | 6/1933 | Henze ..................................... 602/32 |
| 3,403,675 | 10/1968 | Carr ........................................ 602/32 |
| 3,643,655 | 2/1972 | Peronti .................................... 600/228 |
| 3,710,783 | 1/1973 | Jascalevich ......................... 600/234 X |
| 3,823,709 | 7/1974 | McGuire ............................. 600/231 X |
| 4,143,652 | 3/1979 | Meier . |
| 4,622,955 | 11/1986 | Fakhrai . |
| 4,702,465 | 10/1987 | McConnell . |
| 5,088,472 | 2/1992 | Fakhrai . |

OTHER PUBLICATIONS

Roos et al, Annals of Surgery, Mar. 19, 1966, pp. 354–358.
Roos et al, Arch Surg, Jul. 19, 1966, vol. 93 pp. 71–74.

Primary Examiner—Jeffrey A. Smith
Attorney, Agent, or Firm—Renner, Otto, Boisselle & Sklar, P.L.L.

[57] ABSTRACT

A surgical retractor includes a rake plate, and plural rakes for applying retractor force to a body. The rakes are pivotably mounted to the rake plate, and the length of the rakes may be adjusted relative to the rake plate. Various connections are provided for connecting the rakes to the rake plate. Also, the rake plate is concave to facilitate placement relative to a surgery cavity of a patient. A method of holding open a surgery cavity includes the placing of the rakes relative to the cavity and adjusting the length of the respective rakes.

17 Claims, 4 Drawing Sheets

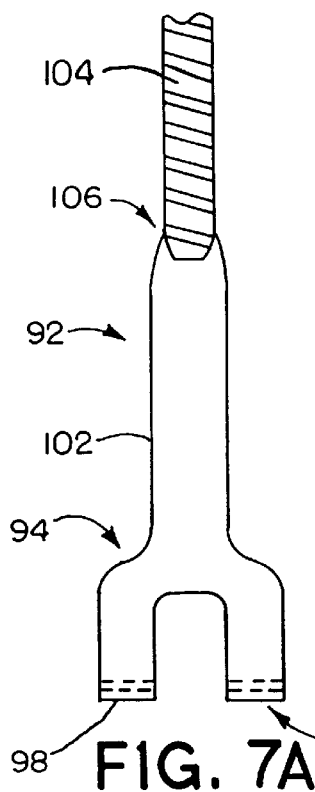
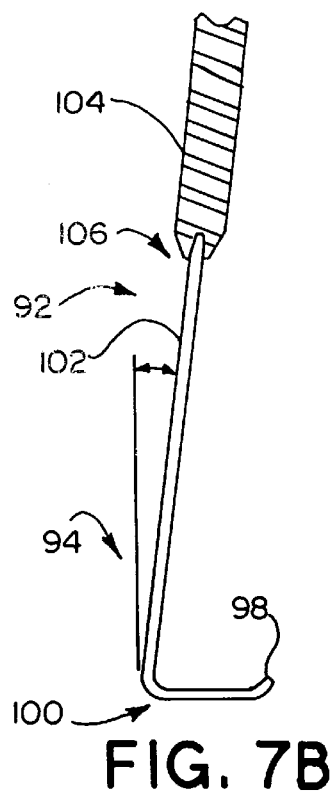
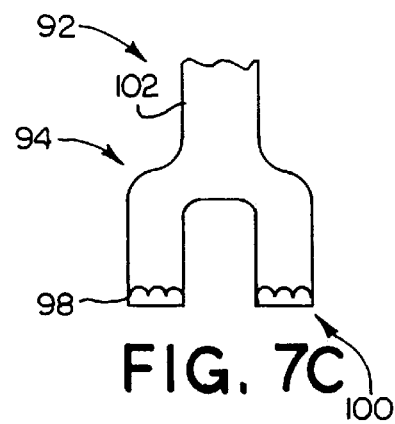
FIG. 7A  FIG. 7B  FIG. 7C
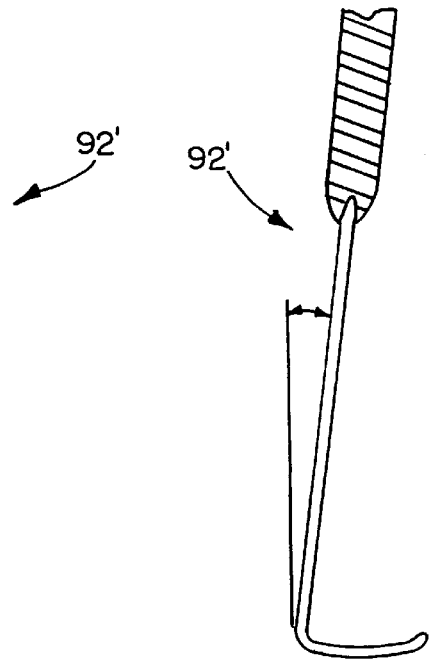
FIG. 8A  FIG. 8B

SURGICAL SUPPORT APPARATUS WITH ADJUSTABLE RAKES AND RAKE PLATE AND METHOD OF USE

TECHNICAL FILED

The present invention relates generally to surgical instruments for holding and elevating body parts and/or for maintaining a clear opening to a body area during surgery.

BACKGROUND OF THE INVENTION

In the performance of surgery in the chest cavity, it is desirable to hold open the cavity (sometimes referred to below as the surgery cavity) for easy access to the organ or body part on which the surgery is being performed. This is especially important in the case of cardiac surgeries. An example of a surgical retractor for dissection of internal mammary artery used for such a purpose is disclosed in U.S. Pat. No. 4,622,955, which is incorporated by reference.

In the device of U.S. Pat. No. 4,622,955 plural rakes which engage the body and pull open the surgery cavity are relatively fixedly positioned with respect to each other from a rod. The rod may be pulled up or let down, as may be desired. However, there is no adjustment for the rakes relative to each other and relative to the surgery cavity.

A copy of FIG. 1 of U.S. Pat. No. 4,622,955 is FIG. 1 of the instant application and is exemplary of a device that can be used to support the support plate of the present invention.

The size and shape of the body of one individual may differ substantially from that of another individual. Also, the size and shape of the opening into a surgery cavity may be different, depending on the patient and the nature of the surgery.

It is well known and appreciated that in surgical procedures, time is of the essence, and delays associated with adjustments of support equipment are unwanted. Additionally, during certain procedures, it may be desirable to impose or to change a biasing force on a body portion which is undergoing a surgical procedure or treatment. Further, it is desirable to minimize the number of personnel required to perform a surgical procedure and to minimize the tasks, such as holding a retractor, of personnel during surgical procedures.

Accordingly, there is a strong need in the art to provide for adjustability for the rakes and rake support structure for such surgical retractor apparatus. It also would be desirable to facilitate the positioning of a retractor apparatus relative to a body and adjustments thereof.

SUMMARY OF THE INVENTION

According to an aspect of the invention, then, a surgical retractor includes a rake plate, plural rakes for applying retractor force to a body, and pivoting mounting means for mounting the rakes to the rake plate.

According to another aspect, a surgical retractor includes a rake plate, plural rakes for applying retractor force to a body, and means for adjusting the extension of the rakes relative to the rake plate.

According to a further aspect, a surgical retractor includes a rake plate, plural rakes for-applying retractor force to a body and mounted with respect to the rake plate, and said rake plate having a generally concave structure.

According to an additional aspect, a surgical retractor includes a rake plate having a center portion and respective end portions, a mount to mount a respective rake in relative proximity to respective end portions of said rake plate, and a clip for coupling a rake in relative proximity to the center portion of the rake plate.

According to another aspect, a method of holding open a surgery cavity includes the placing of a rakes relative to the cavity and adjusting the length of respective rakes.

To the accomplishment of the foregoing and related ends, the invention then comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

In the drawings:

FIGS. 7A, 7B and 7C are, respectively, fragmentary front elevation, side, and back elevation views of a sternal rake useful in accordance with the invention; and FIGS. 8A and 8B are, respectively, fragmentary front elevation and side views of a rib rake useful in accordance with the invention.

DESCRIPTION

Figure 1:
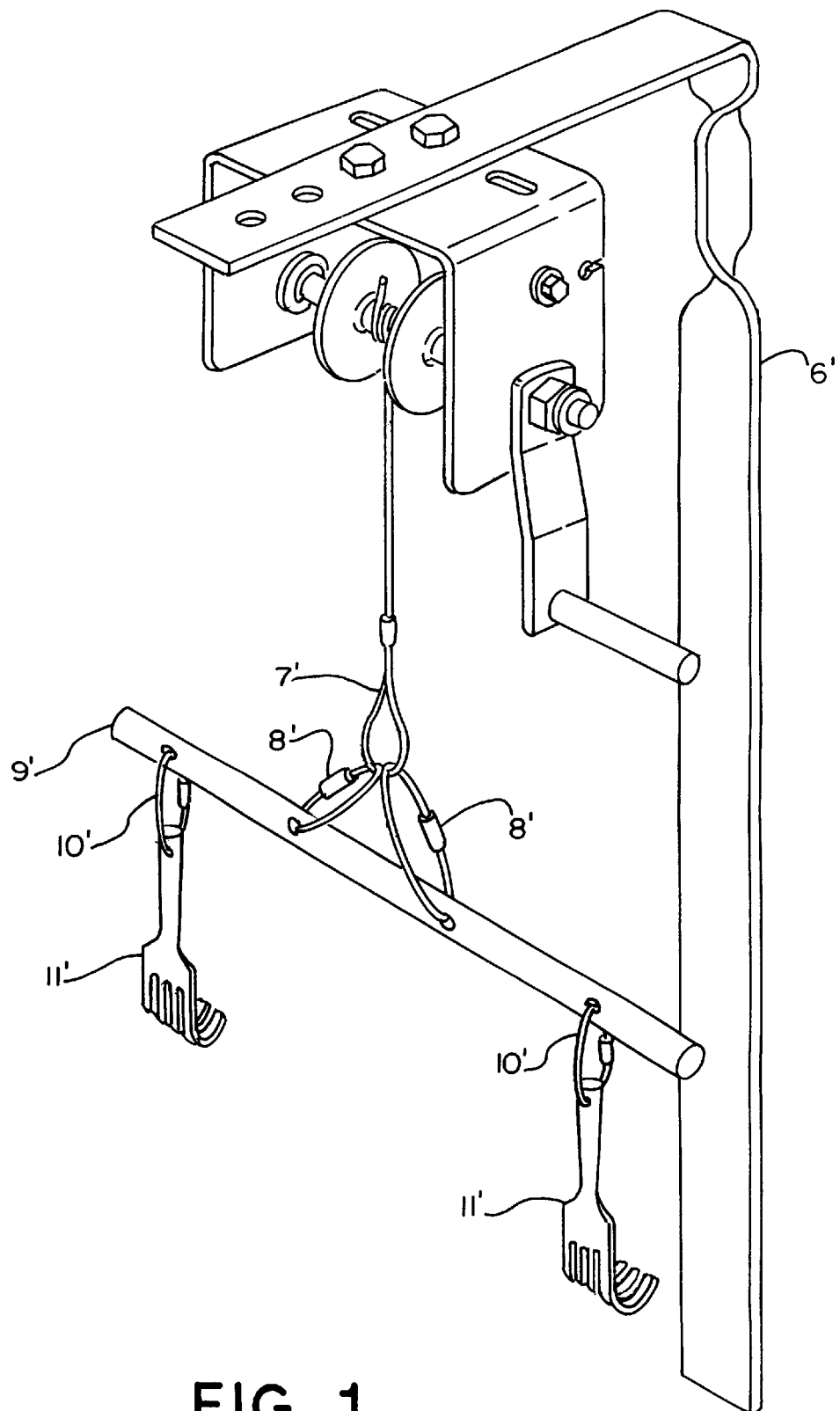
FIG. 1 is an illustration of a surgical retractor for dissection of internal mammary artery of U.S. Pat. No. 4,622,955 with which the present invention may be employed.

The present invention will now be described with reference to the drawings wherein like reference numerals are used to refer to like elements throughout. As mentioned above, the present invention relates to surgical instruments for holding to a body part during surgery, for example, to maintain open and clear a surgery cavity during surgery, such as cardiac surgery or other surgery.

Referring to FIG. 1, the parts thereof are identified by primed reference numerals and correspond to parts in U.S. Pat. No. 4,622,955, which has been incorporated by reference. For further description of the parts so referenced attention is invited to such patent. The rake plate of the present invention, as described in further detail below, may be supported from the cable or cord 7' illustrated in such patent. It will be appreciated that other means also may be used to support the rake plate.

Figure 2:
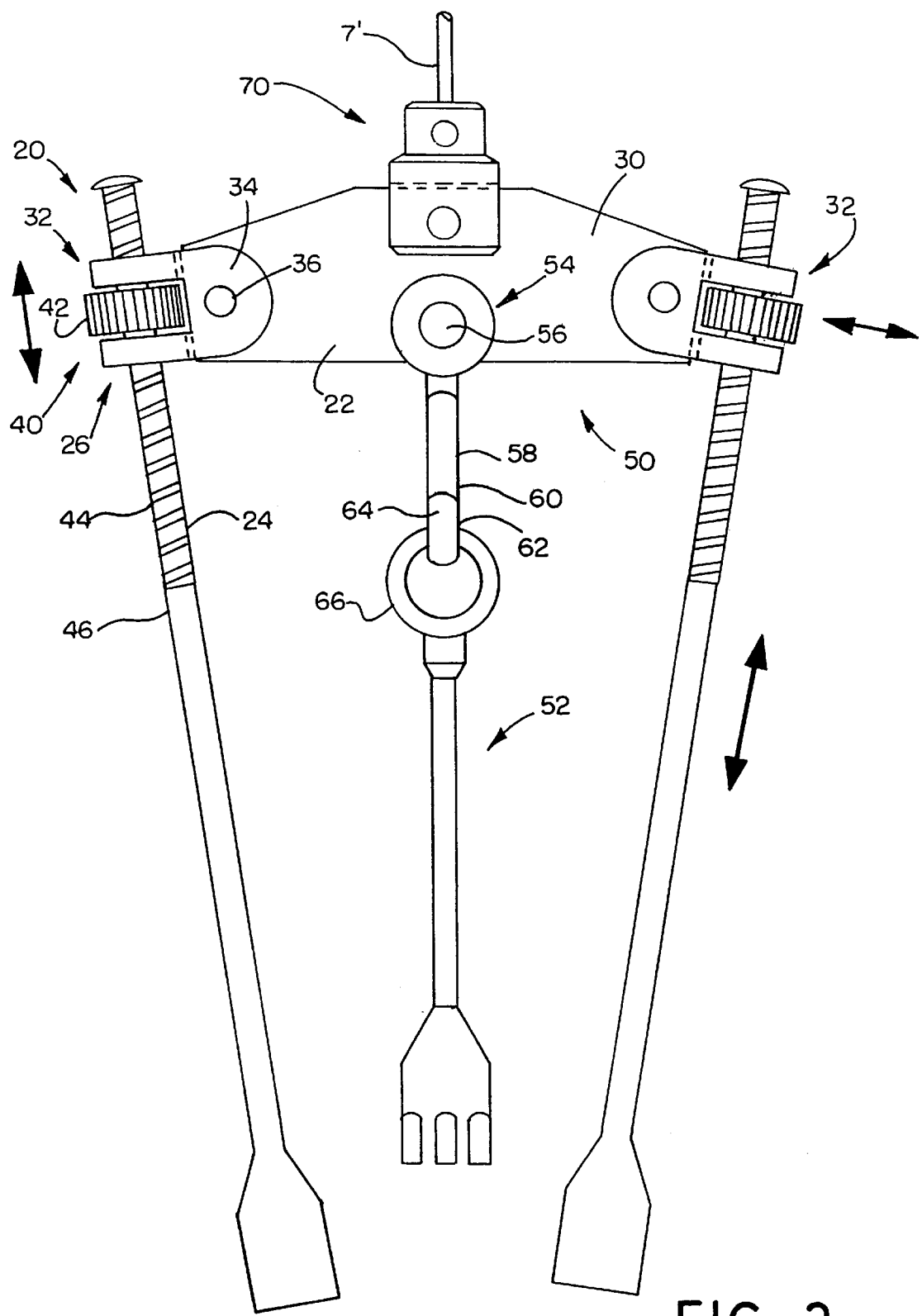
FIG. 2 is a front elevation view of an embodiment of retractor apparatus in accordance with the invention.

A surgical retractor 20 in accordance with the present invention is illustrated in FIG. 2. The surgical retractor 20 includes a rake plate 22, plural rakes 24 for applying retractor force to a body, and a pivoting mounting means 26 for mounting the rakes to the rake plate.

Figure 4:
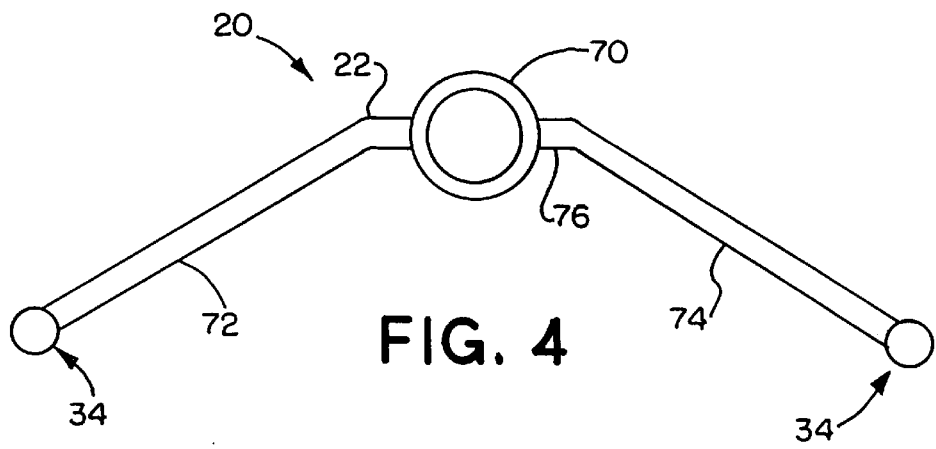
FIG. 4 is a top view of the rake plate of FIG. 2.

The rake plate includes a body 30, which is generally concave, or U-shape, or V-shape, etc., as is illustrated in the top view of FIG. 4. This allows the user to position the rakes 24 at desired locations about the surgery cavity.

At the edges of the rake plate 22 are pivot connections 32 which allow the rakes 24 mounted thereon and thereby to the rake plate to be pivoted angularly for proper positioning with respect to a patient and the surgery cavity thereof. The pivot connections may be a pair of clamps 34 illustrated with a pivot screw, pin, etc. 36 to hold the same to the rake plate body.

The pivot clamps 34 have height adjusters 40 therein. As is illustrated exemplary height adjusters include a threaded nut or the like 42 and a mating thread 44 on the shaft 46 of the rake 24, as is illustrated. By turning the threaded nut which is captured by in the clamp 34, the rake 24 can be raised or lowered relative to the rake plate.

At the center of the rake plate 22, or elsewhere, as may be desired, is a connector 50 for a further rake 52. The connector 50 in the illustrated embodiment is a snap clip that fits into or snaps into a pivot clamp 54 that is attached by a pivot pin or screw 56 to the rake plate 22. The snap connection 58 is a conventional one and allows for different connectors 50 to be attached to the rake plate, for example, connectors of different respective lengths.

At the distal end 60 of the connector 50 relative to the snap connection 58 is a hook or other connection mechanism 62 for coupling with the further rake 52. In the illustrated embodiment the connection mechanism is a hook-like structure 64 that couples to a ring-like structure 66 of the further rake 52. If desired other types of relatively quick connection and release arrangements can be used to quickly and securely couple a further rake 52 to the rake plate 22 and/or to remove the further rake therefrom.

At the top of the rake plate 22 is a pivot hub connector 70 which is connectable to a cable 7' of a support structure, such as that disclosed in the above-mentioned patent. The rake plate 22 and the rakes associated therewith may be raised or lowered via the cable, e.g., in a manner similar to that disclosed in the mentioned patent. Preferably the pivot hub connector 70 allows the rake plate 22 to rotate relative to the cable to facilitate positioning of the rakes relative to the surgery cavity of the patient without twisting the cable 7'.

Figure 3:
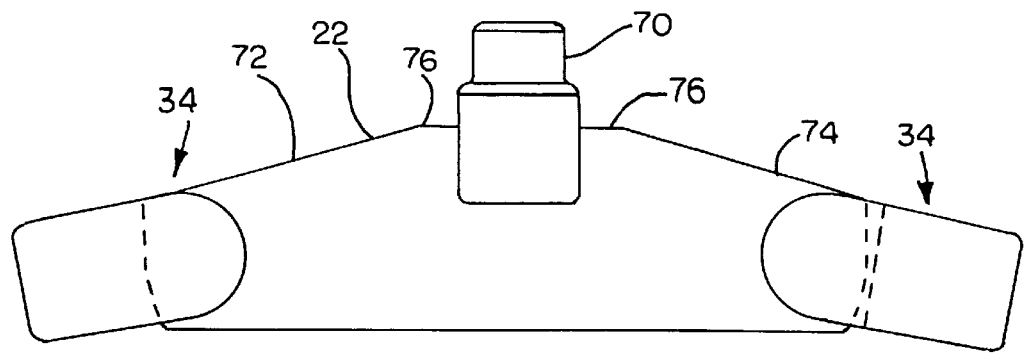
FIG. 3 is an enlarged front view of the rake support plate of the retractor apparatus of FIG. 2.

As is illustrated in FIGS. 3 and 4, the angle of the arms 72, 74 of the rake plate relative to the center portion 76 thereof is about 30 degrees, and preferably the pivot clamps 34 also permit pivot movement on the order of about 30 degrees. However, it will be appreciated that the respective angular relationships may be more or less than those mentioned and illustrated.

Figure 5:
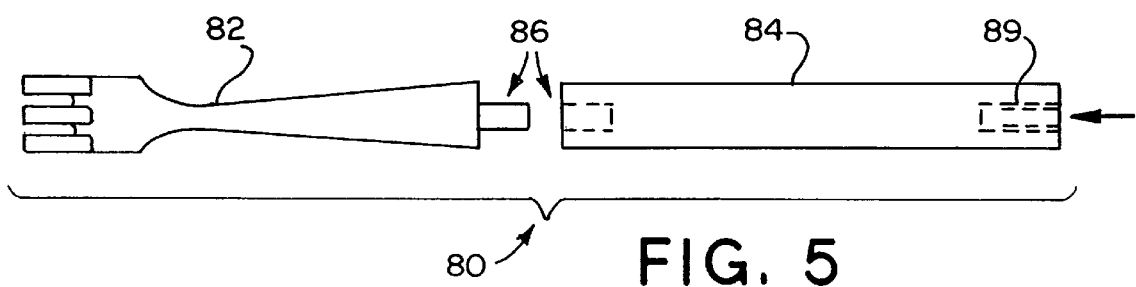
FIG. 5 is an exploded view of a rake and a rake extension useful in the retractor apparatus of the invention.

In FIG. 5 is illustrated an exploded view of a rake 80 which may be used as a rake 24 or as a further rake 52. Such rake 80 has a rake body 82 and an extension 84 which may be screwed to or snapped to the rake body. The connection between the rake body 82 and extension 84 is illustrated at 86. By substituting respective extensions, the length of the rake 80 can be altered conveniently. Also, by substituting an extension that is non-linear or is some specific shape; or a rake of a specific shape with a desired extension, many variables in length, shape, strength, size (e.g., possibly different shape rakes would be used for different size patients) and/or other characteristics for the rake. At an end of the extension 84 is a threaded, snap or other connector 89 to connect the rake directly to the rake plate 22 or via some other mechanism, such as another extension, hook, threaded arm, snap, etc., e.g., as is elsewhere described herein or by some other means.

Figure 6:
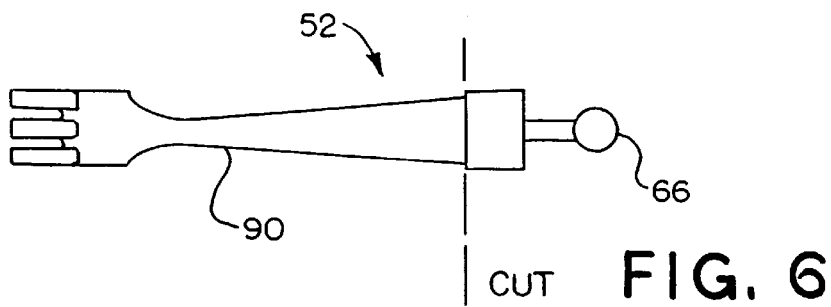
FIG. 6 is a plan view of a further rake with a ring connector attached thereto.

In FIG. 6 is illustrated a further rake 52 with a ring connector 66 to fit on the connector 50. The ring connector 66 may be integral with the further rake 52 or it may be a snap on type of fitting, a screwed on type of fitting, or some other type of fitting to connect to the main body 90 of the further rake 52.

FIGS. 7A, 7B and 7C are, respectively, fragmentary front elevation, side, and back elevation views of a sternal rake 92 useful as one of the rakes 24 or further rake 52 in accordance with the invention. The rake 92 has a distal portion 94 configured to fit into the surgery cavity. The distal portion 94 may be bifurcated, as is illustrated. A roughened, knurled, etc. leading edge 98 of the front 100 of the rake provides a secure grasping of the flesh, skin, or the like of the patient. The stem 102 of the rake 92 relative to the front 100 may be at an angle of about 80 degrees, e.g., about 10 degrees off from a right angle. This angular relationship helps assure easy placement and secure holding to the patient. Other angles also may be used, as desired. The stem 102 of the rake 92 is attached to the threaded extension portion 104 of the rake. The threaded portion may be connected to the threaded nut 42 in the clamp 34 which are described above. The connection 106 of the rake stem 102 and the rake threaded extension portion 104 may be by welding, adhesive, soldering, snap-fit, or other mechanical attachment. If desired, the rake 92 may be made from a single integral piece shaped to the configuration illustrated.

An example of a non-bifurcated rake 92' is illustrated in FIGS. 8A and 8B. The rake 92' may be substantially the same as the rake 92. Either or both of the rakes 92, 92' may be used for the rake 24 or the further rake 52 described above.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A surgical retractor, comprising
   a rake plate having a center portion and respective end portions and defining a generally concave structure,
   at least two rakes for applying retractor force to a body, one of the rakes pivotally mounted to the rake plate at each end portion and
   a pivot hub connector at the center portion of the rake plate, the pivot hub connector rotatably attached to a support structure.

2. A surgical retractor as set forth in claim 1, further comprising means for adjusting the extension of the rakes relative to the rake plate.

3. A surgical retractor as set forth in claim 2, wherein the means for adjusting is a threaded height adjuster.

4. A surgical retractor as set forth in claim 2, wherein the length of each rake is independently adjustable relative to the rake plate.

5. A surgical retractor as set forth in claim 1, wherein said pivotally mounted rakes have a relative pivotal movement of about 30 degrees above and below the end portions.

6. A surgical retractor as set forth in claim 1, further comprising a connector for coupling a third rake in relative proximity to the center portion of the rake plate.

7. A surgical retractor as set forth in claim 6, wherein the connector is a quick connect device.

8. A surgical retractor as set forth in claim 7, wherein the device includes a hook.

9. A surgical retractor as set forth in claim 7, wherein the device includes a ring.

10. A surgical retractor as set forth in claim 1, wherein the pivot hub connector is attached to the support structure by a cable.

11. A surgical retractor as set forth in claim 10, wherein the cable is operably attached to a crank mechanism for raising and lowering the rake plate relative to the support structure.

12. A surgical retractor as set forth in claim 11, wherein the crank mechanism includes a ratchet.

13. A surgical retractor as set forth in claim 1, wherein the concave structure is defined by a plane formed by the end portions and the center portion, in which the plane is perpendicular to a direction defined by a longitudinal axis of the hub connector.

14. A surgical retractor as set forth in claim 1, wherein the concave structure is symmetrically disposed about a longitudinal axis of the hub connector.

15. A method of holding open a surgery cavity including the steps of placing a rake plate having at least two rakes relative to the cavity;

placing each rake relative to the cavity; independently adjusting the length of each of the rakes relative to the rake plate; and lifting the rake plate.

16. A method as in claim 15, wherein the step of lifting the rake plate is by a ratcheting crank mechanism.

17. A method as in claim 15, further including the step of pivotally adjusting the position of each rake relative to the cavity.

* * * * *